United States Patent [19]
Evers et al.

[11] Patent Number: 5,396,079
[45] Date of Patent: Mar. 7, 1995

[54] FIBER OPTIC DETECTOR AND DEPTH SENSOR AND METHOD FOR DOING SAME

[75] Inventors: Lawrence W. Evers, Lake Linden; Kenneth J. Jackson, Dearborn, both of Mich.

[73] Assignee: Board of Control of Michigan Technological University, Houghton, Mich.

[21] Appl. No.: 88,545

[22] Filed: Jul. 6, 1993

Related U.S. Application Data

[63] Continuation-in-part of Ser. No. 794,452, Nov. 19, 1991, abandoned.

[51] Int. Cl.⁶ ............................................. G01N 21/49
[52] U.S. Cl. ..................... 250/577; 250/903; 250/227.25; 250/227.28
[58] Field of Search ............... 250/903, 904, 905, 576, 250/577, 227.21, 227.2, 227.25, 227.28; 385/12; 340/619

[56] References Cited

U.S. PATENT DOCUMENTS

| | | | |
|---|---|---|---|
| 4,039,845 | 8/1977 | Oberhänsli et al. | 250/577 |
| 4,240,751 | 12/1980 | Linnecke et al. | 250/227.11 |
| 4,320,291 | 3/1982 | Uramoto et al. | 250/903 |
| 4,713,552 | 12/1987 | Denis et al. | 250/903 |
| 4,909,588 | 3/1990 | Harner et al. | 385/12 |
| 4,998,022 | 3/1991 | Tregay | 250/903 |

*Primary Examiner*—David C. Nelms
*Assistant Examiner*—Stephone B. Allen
*Attorney, Agent, or Firm*—Michael, Best & Friedrich

[57] ABSTRACT

A fiber optic sensor for determining the presence and/or measuring the depth of a first substance capable of transmitting light. The fiber optic sensor includes a plurality of light receiving fibers, a plurality of light transmitting fibers surrounding the light receiving fibers and structure for refracting light from the light transmitting fibers at a predetermined angle for total internal reflection of the light from an interface of the first substance with a second substance.

28 Claims, 4 Drawing Sheets

FIBER OPTIC DETECTOR AND DEPTH SENSOR AND METHOD FOR DOING SAME

This application is a continuation-in-part of application Ser. No. 794,452, filed Nov. 19, 1991, and now abandoned.

FIELD OF THE INVENTION

The invention relates to fiber optic sensors.

BACKGROUND OF THE INVENTION

Generally, fiber optic converters are used for measuring small displacements of objects subjected to vibrations. Examples of such fiber optic converters are disclosed Poilleux U.S. Pat. No. 3,792,298, Tourret U.S. Pat. No. 3,771,873 and Brelot et al. U.S. Pat. No. 3,778,157. In these patents, fiber optic bundles are used to transmit and receive a light beam reflected off a surface for measuring the thickness or depth of a layer of a first substance. A characteristic response curve is determined from the parameters of the system. A reflected value is compared to the response curve to determine the thickness of the layer.

One disadvantage of the above fiber optic converters is that the critical angle of the interface of the first substance with a second substance is not used. The critical angle is the angle at which light rays must impact upon the interface in order for the light rays to be totally internally reflected by the interface. Another disadvantage is that these converters do not rely upon total internal reflection of light from the interface. A further disadvantage is that these converters must be mounted above the substance to be measured, thus, these converters cannot be used in blind applications.

SUMMARY OF THE INVENTION

The invention is a fiber optic sensor including a plurality of light receiving fibers and a plurality of light transmitting fibers surrounding the light receiving fibers. The sensor includes means for refracting light exiting the light transmitting fibers at a predetermined angle to allow light rays which impact an interface between a first substance and a second substance to be totally internally reflected by the interface and enter the light receiving fibers. The sensor is capable of detecting the presence of the first substance and also capable of measuring the thickness or depth of that first substance.

It is one feature of the invention to provide a fiber optic sensor capable of determining the presence of a substance.

It is another feature of the invention to provide a fiber optic sensor capable of measuring the thickness or depth of a substance.

It is another feature of the invention to provide a fiber optic sensor having light transmitting fibers surrounding light receiving fibers.

It is another feature of the invention to provide a fiber optic sensor which relies upon total internal reflection of light from an interface of a first substance and a second substance.

It is another feature of the invention to provide a fiber optic sensor which uses the critical angle at the interface of a first substance and a second substance to determine the presence of the first substance.

It is another feature of the invention to provide a fiber optic sensor which uses the critical angle at the interface of a first substance and a second substance to determine the thickness of the first substance.

It is another feature of the present invention to provide a fiber optic sensor which is utilized from the underside of the substance to be detected or measured.

Other objects, features and advantages of the invention will become apparent to those of ordinary skill in the art upon review of the following drawings, detailed description, and claims.

DESCRIPTION OF THE PREFERRED EMBODIMENTS

Figure 1:
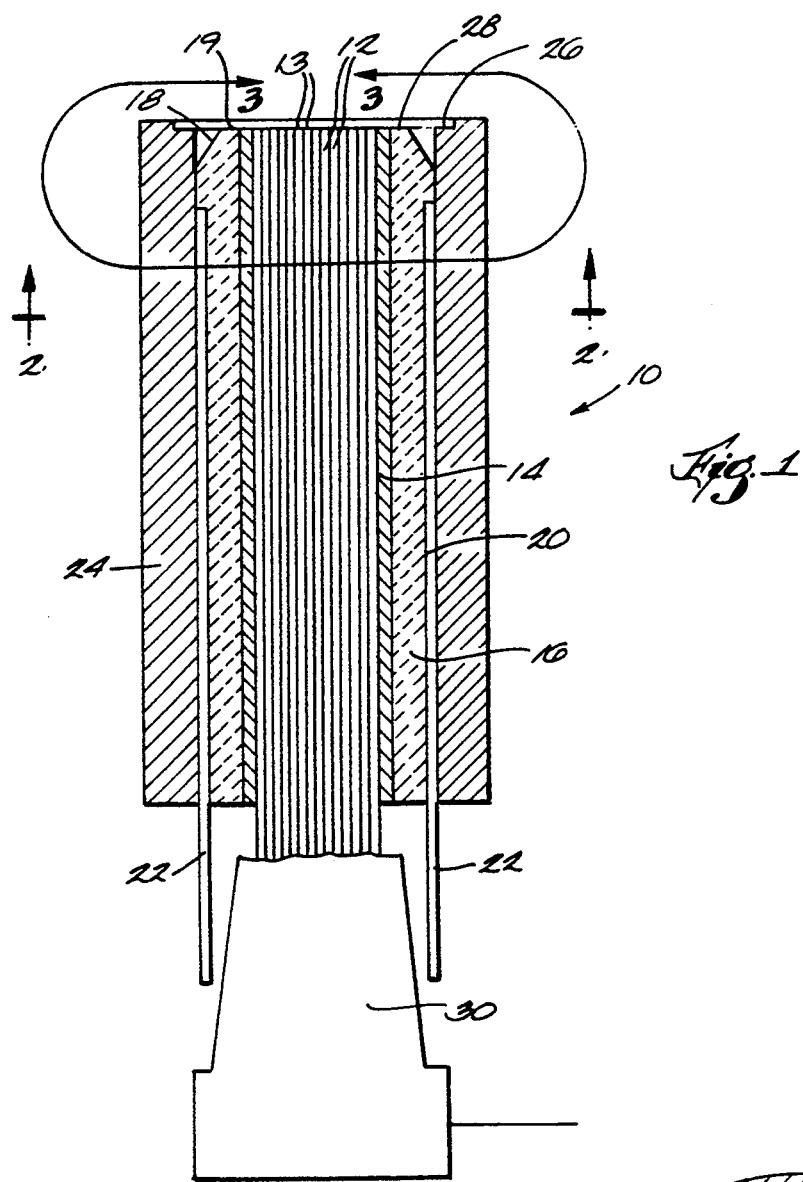
FIG. 1 is a fragmentary elevational view of a fiber optic sensor embodying the invention.
Figure 2:
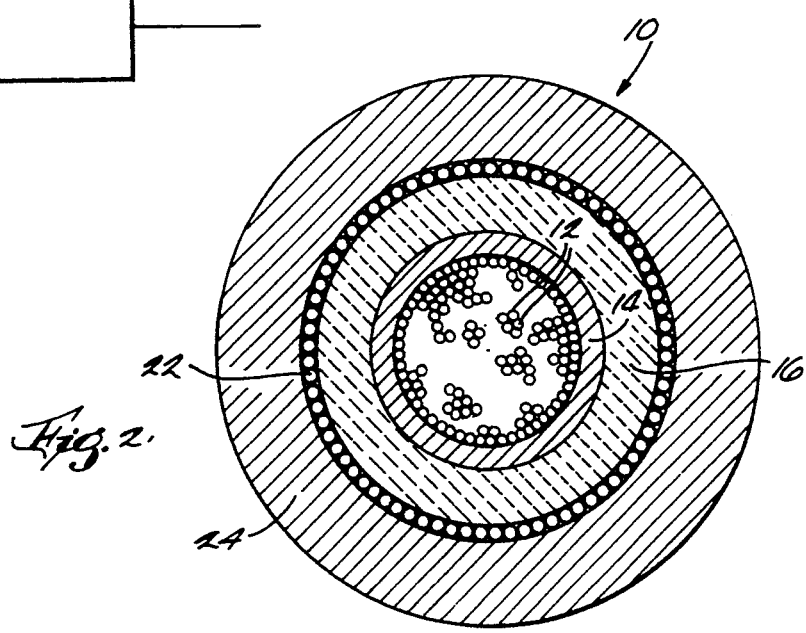
FIG. 2 is a sectional view taken along line 2—2 of FIG. 1.

Referring to FIGS. 1 and 2, a fiber optic sensor 10 according to the present invention is shown. The sensor 10 includes at least one, preferably a plurality, of optical or light receiving fibers 12. The receiving fibers 12 are arranged in a bundle and act as an image conduit. Preferably, the receiving fibers 12 are made of a transparent material such as glass and are formed into a substantially solid circular bundle in cross-section. Each of the receiving fibers 12 has an end 13 and each end 13 is preferably straight and aligned to terminate in substantially the same plane with the other ends 13. A photodetector such as a photodiode 30 is connected to the receiving fibers 12 and converts light received by the receiving fibers 12 to an electrical signal. The output of the photodiode 30 is a current that is proportional to the light received by the photodiode. A tubular sheath 14 encompasses the receiving fibers 12. Preferably, the sheath 14 is composed of a metal such as aluminum and has a diameter of 0.15625 inches. One end of the sheath 14 is aligned with the ends 13 of the receiving fibers 12 and the receiving fibers 12 extend through and beyond the other end of the sheath 14.

The sensor 10 further includes a reflector 16. Preferably, the reflector 16 is made of a transparent material such as plexiglass. The reflector 16 has an inclined surface 18 near one end 19 which forms a general cone shape. The end 19 is aligned with the ends 13 of the receiving fibers 12. The reflector 16 has a recess 20 in its outer periphery which extends from the end opposite end 19 to prior to the inclined surface 18. The inclined surface 18 is at a predetermined angle based upon the critical angle of an interface of two selected light transmitting substances. The critical angle is the angle at which light rays must pass through the first substance and impact upon the interface of the first and a second substance in order for the light rays to be totally internally reflected from the interface, i.e., sent back through the first substance without passing into the second substance. It should be appreciated that the surfaces of the reflector 16 that are not used to transmit light may be covered such as by painting to prevent stray light from being transmitted.

Continuing to refer to FIGS. 1 and 2, the sensor 10 includes at least one, preferably a plurality of, optical or light transmitting fibers 22. The transmitting fibers 22 are disposed in the recess 20 and arranged in series to form a circular configuration, preferably forming a concentric circular array to the receiving fibers 12. Preferably, the transmitting fibers 22 are made of a transparent material such as glass with a diameter greater than the diameter of the receiving fibers 12. The ends of the transmitting fibers 22 that transmit light are preferably straight or planar. The other ends of the transmitting fibers 22 are connected to a light source to be later described. Encompassing the transmitting fibers 22 is a housing 24. The housing 24 is tubular and preferably made of a metal such as aluminum with a diameter of 0.375 inches. The housing 24 has a recess 26 at one end. Disposed in the recess 26 is a cover 28. The cover 28 is preferably made of a transparent material such as glass with a thickness of 0.007 inches. The cover 28 is secured to the housing 24 by suitable means such as epoxy. It should be appreciated that the cover 28 separates the reflector 16 from the first substance which is to be detected or measured.

Figure 3:
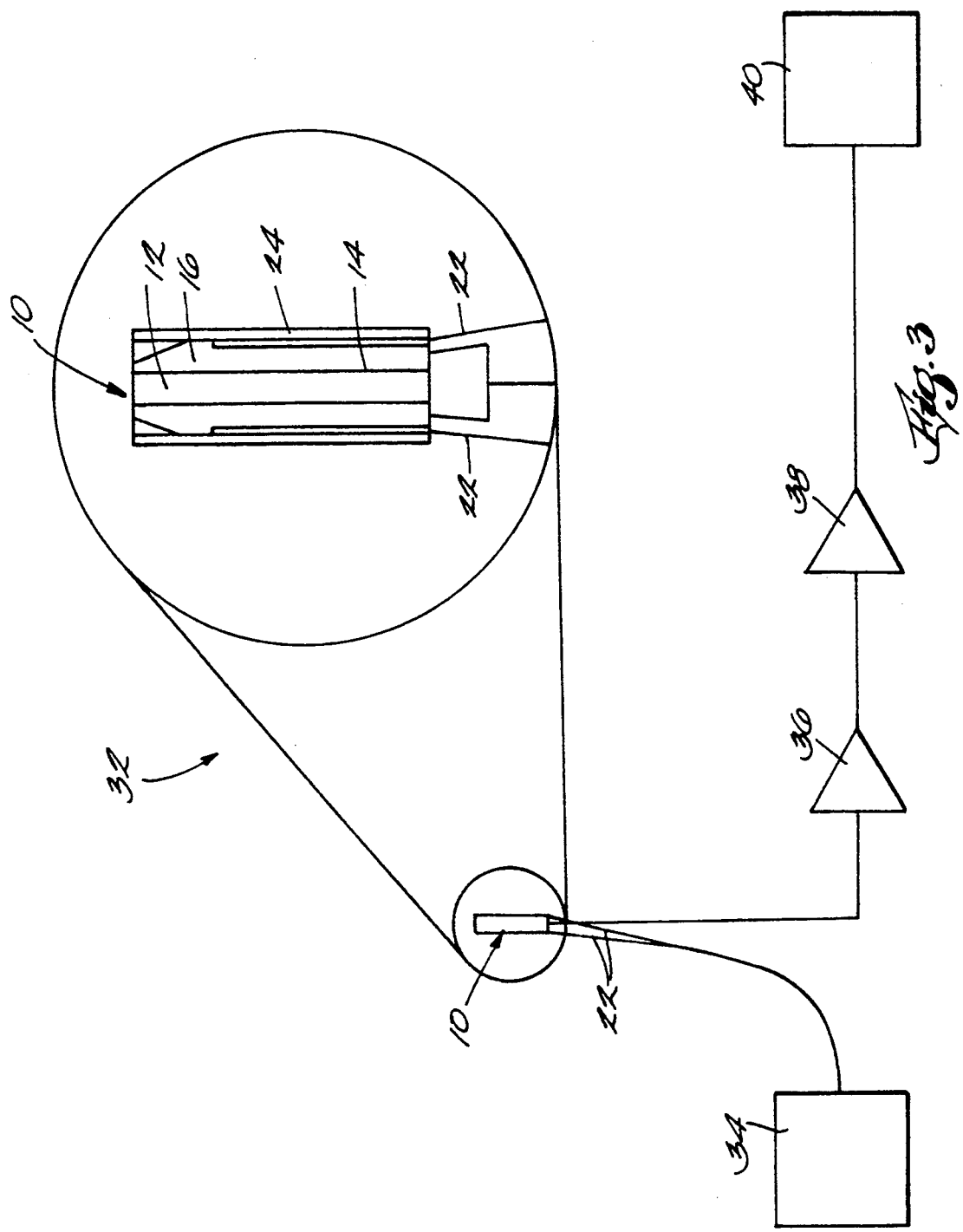
FIG. 3 is a schematic view of a system incorporating the fiber optic sensor.

Referring to FIG. 3, a system 32 is shown which includes the sensor 10 and a light source 34 which is connected to the transmitting fibers 22. The light source 34 may be either a DC powered source, an AC powered source with no time variation of the light output, or a laser light source. A transimpedence amplifier 36 is connected to the photodiode 30 and converts the current from the photodiode 30 into a voltage. The transimpedence amplifier 36 may be a LF 355 operational amplifier having variable feedback resistance as disclosed in the "Handbook of Operational Amplifier Circuit Design" by D. F. Stout. A voltage divider 38 is connected to the amplifier 36 for providing a zero adjustment. The voltage divider 38 may be of the type known as a non-inverting summing junction. A display/recording device 40 is connected to the voltage divider 38 to record the voltage output of the system 32.

Figure 4:
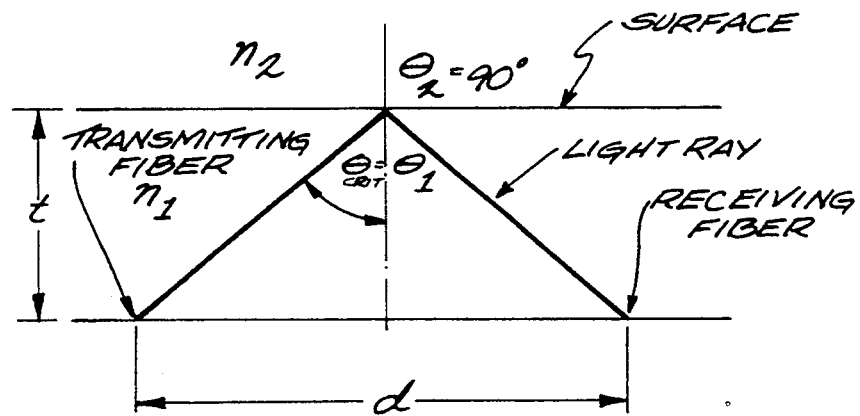
FIG. 4 is a view illustrating the transmission and reception of light from an interface of a first substance $n_1$ and a second substance $n_2$.

Referring to FIG. 4, the sensor 10 operates based on Snell's law. Snell's law states:

$$n_1 \sin\theta_1 = n_2 \sin\theta_2$$

This is the fundamental form of Snell's law where $n_1$ and $n_2$ are the indices of refraction for a first and a second substance. For example, $n_1$ may be water and $n_2$ may be air or $n_1$ may be ice and $n_2$ may be air. $\theta_1$ is the incident angle and $\theta_2$ is the angle of refraction as illustrated in FIG. 4. The equation for the critical angle is thus derived by setting $\theta_2$, the angle for the incident ray, equal to ninety (90) degrees. The equation that results is:

$$\theta_{crit} = \sin^{-1} \frac{(n2)}{n_1}$$

This is the relationship for the angle necessary for total internal reflection of light for two substances with different refractive indices. Any light impacting the interface at an angle equal to or greater than the critical angle ($\theta_{crit}$) will be completely reflected by the interface, i.e., will not travel through the second substance. For example, when the sensor 10 is disposed in a substance such as water and the water interfaces with air, the critical angle is forty-two (42) degrees from a longitudinal axis of the reflector 16.

The system 32 operates in two modes, as a detecting device and as a thickness measuring device. In its operation as a detecting device, the system 32 determines whether or not a substance is present on a surface. For example, the system 32 can determine whether or not ice has formed on airplane wings. In this application, the sensor 10 is implanted in the airplane wing flush with the outer surface of the wing. When the sensor 10 is operating, light is emitted by the light source 34 to the transmitting fibers 22 and the transmitting fibers 22 transmit light through the reflector 16 toward the inclined surface 18. The inclined surface is inclined at an angle equal to or greater than the critical angle which was determined for a ice/air interface using the above stated formula. Light rays strike the inclined surface 18 and are refracted by the inclined surface 18 and sent through end 19, and cover 28. If ice is present on the airplane wing surface, the refracted light passes through the ice and strikes the ice/air interface. Because the light rays have been refracted by inclined surface 18 at an angle equal to or greater than the critical angle, the light rays will be totally internally reflected by the interface and sent back toward the receiving fibers 12. The receiving fibers 12 provide the received light to the photodiode 30. The photodiode 30 produces a current which is converted by the amplifier 36 to a voltage. If the voltage exceeds a calibrated threshold level, i.e., if enough light has entered the receiving fibers 12, the determination can be made that there is ice present on the surface of the airplane wing.

Alternatively, if ice is not present, the light rays exiting the transmitting fibers 22 will not be reflected by any interface, hence, the light receiving fibers will not be receiving the necessary amount of light to exceed the threshold voltage level and the determination can be made that ice is not present. It should be appreciated that the system 32 including the sensor 10 can be used in other applications for detecting whether a light transmitting substance is present in additional to the airplane wing example set forth above.

In its second mode, the system 32 including the sensor 10 operates to measure the thickness or depth of a light transmitting substance such as a fluid or a solid. For example, the system 32 can measure the thickness of an oil film on a cylinder wall of a running engine. In this application, the sensor 10 is implanted flush with the cylinder wall. Light is emitted from the light source 34 to the transmitting fibers 22 which transmit the light through the reflector 16 toward the inclined surface 18. The inclined surface is inclined at an angle equal to or greater than the critical angle which was determined for the oil/air interface using the above stated formula. The light rays are refracted by the inclined surface 18 and sent through end 19, cover 28 and the layer of oil. Because the light rays were refracted by the inclined surface 18 at an angle equal to or greater than the critical angle, the light rays will be totally internally reflected by the oil/air interface and sent back toward the receiving fibers 12. The receiving fibers 12 provide the received light to the photodiode 30. The photodiode 30 produces a current which is converted by the amplifier 36 to a voltage.

As illustrated in FIG. 4, t is the thickness or depth of the substance to be measured such as oil in this example and d is the distance between the transmitting fibers 22 and the receiving fibers 12. This distance d may be known or determined by conventional methods such as recording ring diameters versus depth. As a result, the depth t of the oil may be determined using the following equation:

$$t = \frac{d \tan \theta_{crit}}{2}$$

This equation provides a linear relationship between the depth of the oil and the distance between the transmitting fibers 22 and the receiving fibers 12 assuming a given angle, $\theta_{crit}$. It should be appreciated that for dynamic measurements a linear response is desired.

Figure 5:
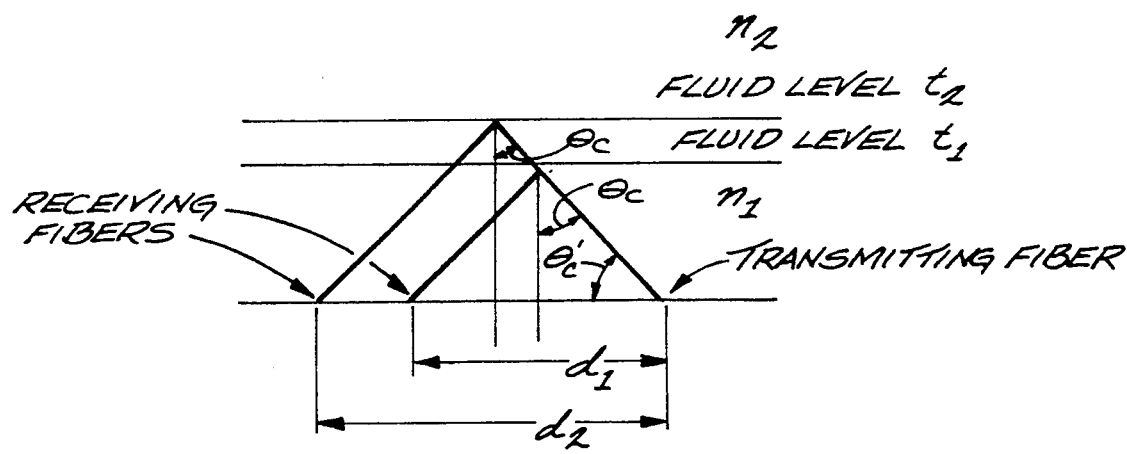
FIG. 5 is a view similar to FIG. 4 illustrating transmission and reception of light from the interface at a first and second predetermined depth.

As illustrated in FIG. 5, the operation of the sensor 10 is shown when the depth of the substance to be measure such as oil changes. The distances $d_1$ and $d_2$ represent known distances between a transmitting fiber 22 and two different receiving fibers 12. Since the light is reflected at the substance $n_2$ at incident angles equal to or greater than the critical angle $\theta_{crit}$, the critical angle $\theta_{crit}$ remains the same but the receiving fiber 12 changes depending upon what oil level $t_1$ and $t_2$ is present. By knowing the distance $d_1$ and $d_2$, the oil level $t_1$ or $t_2$ can be calculated. Thus, very accurate calculations and changes of thicknesses can be determined.

Figure 6:
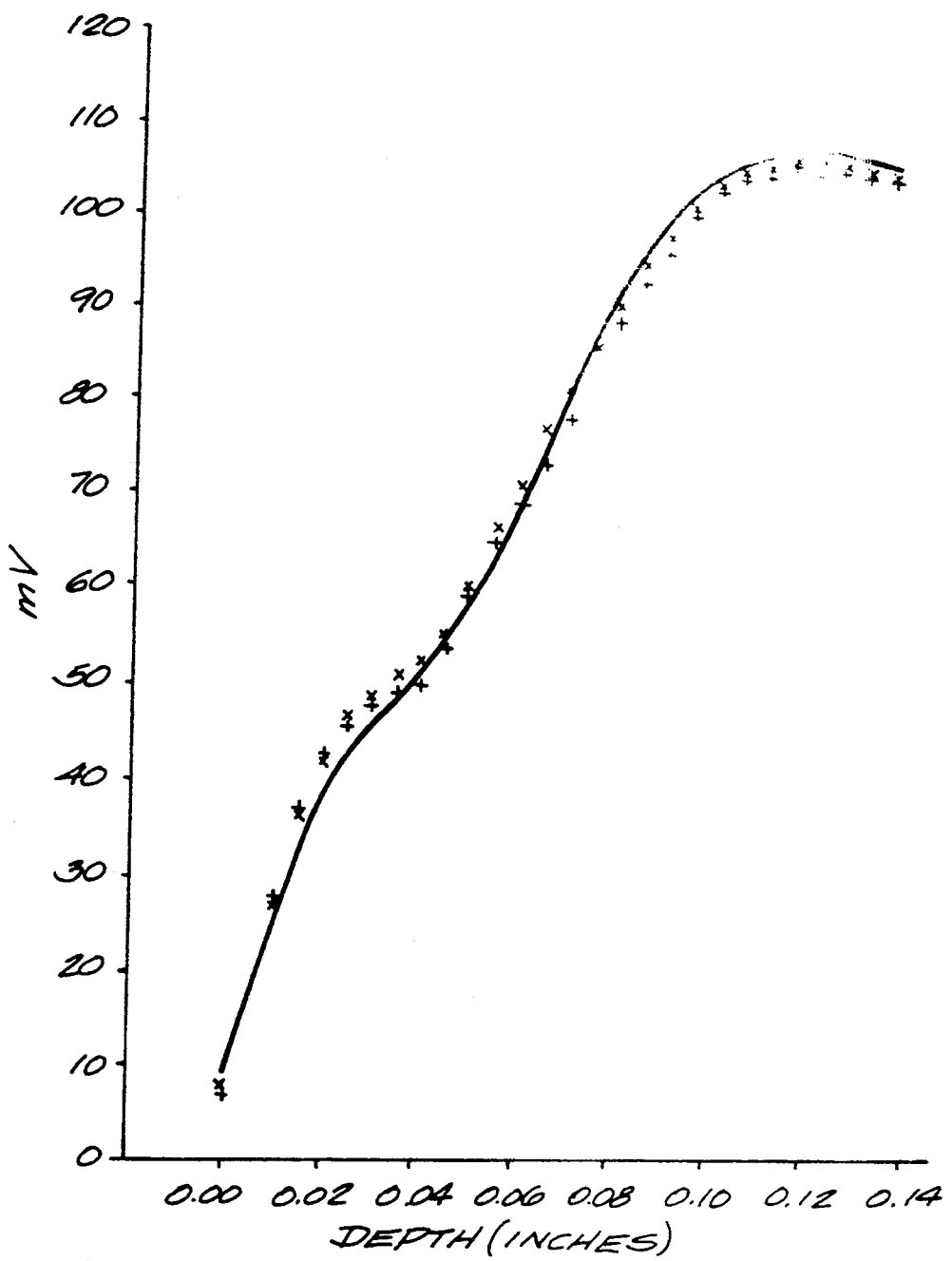
FIG. 6 is a graph of a voltage versus depth curve for the fiber optic sensor used in water with a water/air interface.

Accordingly, the system 32 may be calibrated to produce a voltage versus depth curve for two known substances. For example, if the sensor 10 is disposed in a substance such as water and the other substance is air, a voltage versus depth curve may be generated as illustrated in FIG. 6. This curve may be used to determine dynamic changes in depth of water based on the voltage output of the sensor 10. It should be appreciated that the sensor 10 may be calibrated for other mediums that are capable of transmitting light.

The advantages of the invention include a relatively simple and inexpensive method of determining the presence and determining thicknesses of substances capable of light transmission. Further, the use of fiber optics enables the ends of the fibers to be placed in a relatively hard to reach or remote area, while the actual sensing equipment is at another remote location at the other end of the fibers. Also, the fiber optic sensor measures the presence and depth of a substance from the underside of that substance allowing the sensor to be used in blind applications.

I claim:

1. A fiber optic fluid depth sensor for measuring the depth a fluid interfacing with a second substance, said sensor comprising:
   a plurality of light receiving fibers;
   a plurality of light transmitting fibers;
   means for transmitting light to said light transmitting fibers; and
   means for refracting light from said light transmitting fibers at a predetermined angle so that light striking the interface of the fluid with the second substance will be totally internally reflected and received by said light receiving fibers.

2. A fiber optic fluid depth sensor as set forth in claim 1 wherein said refracting means includes a reflector disposed between said light receiving fibers and said light transmitting fibers.

3. A fiber optic fluid depth sensor as set forth in claim 2 wherein said reflector includes an inclined surface with respect to an optical axis at said predetermined angle.

4. A fiber optic fluid depth sensor as set forth in claim 1 including means receiving the light from said light receiving fibers for producing a current proportional to the light received.

5. A fiber optic fluid depth sensor as set forth in claim 4 wherein said receiving means includes a photodiode.

6. A fiber optic fluid depth sensor as set forth in claim 1 including a sheath disposed about said light receiving fibers to form a bundle.

7. A fiber optic fluid depth sensor as set forth in claim 1 including a housing encompassing said light transmitting fibers.

8. A fiber optic fluid depth sensor as set forth in claim 7 wherein said housing includes a recess at one end.

9. A fiber optic fluid depth sensor as set forth in claim 8 including a cover disposed in said recess.

10. A method of measuring the depth of a fluid using a fiber optic fluid depth sensor, said method comprising the steps of:
    surrounding a plurality of light receiving fibers with a plurality of light transmitting fibers in a fiber optic fluid depth sensor;
    disposing the fiber optic fluid depth sensor in a first fluid;
    transmitting light from a light source through the transmitting fibers;
    refracting light from the transmitting fibers at a predetermined angle toward an interface between the first fluid and a second fluid;
    reflecting light from the interface at an angle equal to or greater than a critical angle of the first and second fluids; and
    receiving the reflected light with the receiving fibers which receive the light by total internal reflection from the interface.

11. A method as set forth in claim 10 and further including the step of converting the light received by the receiving fibers into an electrical current.

12. A method as set forth in claim 11 and further including the step of converting said electrical current into an electrical voltage.

13. A method as set forth in claim 12 and further including the step of comparing said electrical voltage to a calibrated curve for voltage output versus depth to determine the depth of the first fluid.

14. A method of measuring the depth of a fluid using a fiber optic fluid depth sensor, said method comprising the steps of:
    surrounding a means of light receiving fibers with a plurality of light transmitting fibers in a fiber optic fluid depth sensor;
    disposing fiber optic fluid depth sensor in a first fluid;
    transmitting light from a light source through the transmitting fibers;
    refracting light from the transmitting fibers at a predetermined angle toward an interface between the first fluid and a second fluid;
    reflecting light from the interface at an angle equal to or greater than a critical angle of the first and second fluids; and
    receiving the reflected light with the receiving fibers which transmit the light by total internal reflection;
    converting the light received by the receiving fibers into an electrical current;
    converting the electrical current into an electrical voltage; and comparing the electrical voltage to a calibrated curve for voltage output versus depth to determine the depth of the fluid measured.

15. A method of determining the presence of a first substance on a surface using a fiber optic sensor, said method comprising the steps of:
   surrounding a plurality of light receiving fibers with a plurality of light transmitting fibers in a fiber optic sensor;
   disposing the fiber optic sensor in the surface;
   transmitting light from a light source through the transmitting fibers;
   refracting light from the transmitting fibers at a predetermined angle so that light strikes any interface that may be present between the first substance and a second substance at an angle equal to or greater than a critical angle for the first and second substances;
   reflecting light from the interface if the first substance is present; and
   receiving the reflected light with the light receiving fibers.

16. A fiber optic sensor for detecting the presence of a first substance, said sensor comprising:
   a plurality of light receiving fibers;
   a plurality of light transmitting fibers;
   means for transmitting light to said light transmitting fibers; and
   means for refracting light from said light transmitting fibers at a predetermined angle toward any interface of the first substance and a second substance whereby if the first substance is present, light from the interface is totally internally reflected by the interface and received by the light receiving fibers.

17. A fiber optic sensor as set forth in claim 16 wherein said refracting means includes an inclined surface.

18. A fiber optic sensor as set forth in claim 16 including means receiving the light from said light receiving fibers for producing a current proportional to the light received.

19. A fiber optic sensor as set forth in claim 18 wherein said receiving means includes a photodiode.

20. A fiber optic depth sensor for measuring the depth of a first substance interfacing with a second substance, said sensor comprising:
   a plurality of light receiving fibers;
   a plurality of light transmitting fibers;
   means for transmitting light to said light transmitting fibers; and
   means for refracting light from said light transmitting fibers at a predetermined angle so that light striking the interface of the first substance with the second substance will be totally internally reflected and received by said light receiving fibers.

21. A fiber optic depth sensor as set forth in claim 20 wherein said refracting means includes a reflector disposed between said light receiving fibers and said light transmitting fibers.

22. A fiber optic depth sensor as set forth in claim 21 wherein said reflector includes an inclined surface with respect to an optical axis at said predetermined angle.

23. A fiber optic depth sensor as set forth in claim 20 including means receiving the light from said light receiving fibers for producing a current proportional to the light received.

24. A fiber optic depth sensor as set forth in claim 23 wherein said receiving means includes a photodiode.

25. A method of measuring the depth of a substance, said method comprising the steps:
   supplying a plurality of light transmitting fibers;
   supplying a plurality of light receiving fibers;
   transmitting light from a light source through the light transmitting fibers;
   refracting light exiting the light transmitting fibers at a predetermined angle;
   transmitting the refracted light through the depth of the substance;
   reflecting the light that travels through the substance when the light strikes an interface between the substance and a second substance;
   receiving the reflected light with the light receiving fibers;
   calculating the depth of the substance based upon the amount of light received by the light receiving fibers.

26. A fiber optic fluid depth sensor as set forth in claim 1 wherein said plurality of light transmitting fibers surrounds said light receiving fibers.

27. A fiber optic sensor as set forth in claim 16 wherein said plurality of light transmitting fibers surrounds said light receiving fibers.

28. A fiber optic depth sensor as set forth in claim 20 wherein said plurality of light transmitting fibers surround said light receiving fibers.

* * * * *